United States Patent
Addiego

[11] Patent Number: 5,917,588
[45] Date of Patent: Jun. 29, 1999

[54] AUTOMATED SPECIMEN INSPECTION SYSTEM FOR AND METHOD OF DISTINGUISHING FEATURES OR ANOMALIES UNDER EITHER BRIGHT FIELD OR DARK FIELD ILLUMINATION

[75] Inventor: Ginetto Addiego, Berkeley, Calif.

[73] Assignee: KLA-Tencor Corporation, San Jose, Calif.

[21] Appl. No.: 08/743,998

[22] Filed: Nov. 4, 1996

[51] Int. Cl.⁶ .................................................. G01N 21/88
[52] U.S. Cl. ............................................................ 356/237
[58] Field of Search ..................... 356/237, 394

[56] References Cited

U.S. PATENT DOCUMENTS

| | | | |
|---|---|---|---|
| 4,247,203 | 1/1981 | Levy et al. | 356/398 |
| 4,347,001 | 8/1982 | Levy et al. | 356/398 |
| 4,500,202 | 2/1985 | Smyth | 356/237 |
| 4,578,810 | 3/1986 | MacFarlane et al. | 382/8 |
| 4,579,455 | 4/1986 | Levy et al. | 356/394 |
| 4,595,289 | 6/1986 | Feldman et al. | 356/237 |
| 4,623,256 | 11/1986 | Ikenaga et al. | 356/394 |
| 4,644,172 | 2/1987 | Sandland et al. | 250/548 |
| 4,898,471 | 2/1990 | Stonestrom et al. | 356/394 |
| 4,943,713 | 7/1990 | Yoshida | 250/223 B |
| 5,058,178 | 10/1991 | Ray | 382/8 |
| 5,076,692 | 12/1991 | Neukermans et al. | 356/237 |
| 5,096,291 | 3/1992 | Scott | 356/237 |
| 5,124,927 | 6/1992 | Hopewell et al. | 364/468 |
| 5,135,303 | 8/1992 | Uto et al. | 356/237 |
| 5,153,444 | 10/1992 | Maeda et al. | 250/562 |
| 5,153,668 | 10/1992 | Katzir et al. | 356/237 |
| 5,173,719 | 12/1992 | Taniguchi et al. | 356/394 |
| 5,216,845 | 6/1993 | Bird et al. | 356/237 |
| 5,235,400 | 8/1993 | Terasawa et al. | 356/237 |
| 5,278,012 | 1/1994 | Yamanaka et al. | 430/30 |
| 5,293,538 | 3/1994 | Iwata et al. | 356/237 |
| 5,392,113 | 2/1995 | Sayka et al. | 356/237 |
| 5,428,442 | 6/1995 | Lin et al. | 356/237 |
| 5,455,870 | 10/1995 | Sepai et al. | 382/147 |
| 5,463,459 | 10/1995 | Morioka et al. | 356/237 |
| 5,473,426 | 12/1995 | Hayano et al. | 356/237 |
| 5,631,733 | 5/1997 | Henley | 356/237 |

FOREIGN PATENT DOCUMENTS

| | | | |
|---|---|---|---|
| 0374694 | 6/1990 | European Pat. Off. | G01N 21/88 |
| 3165534 | 7/1991 | Japan | H01L 21/66 |
| 9200517 | 1/1992 | WIPO | G01N 21/89 |
| 9418643 | 8/1994 | WIPO | G06K 9/00 |

*Primary Examiner*—Robert Kim
*Assistant Examiner*—Zandra V. Smith

[57] ABSTRACT

An automated inspection system and method replaces human visual inspection of the surface of a specimen having distinguishing features or anomalies that are detectable under either one or a combination of bright field and dark field illumination. A preferred embodiment is an after develop inspection macro (ADI Macro) defect inspection system that inspects the patterned surface of a semiconductor wafer for large scale (i.e., greater than about 25 micron minimum dimension range) defects. The ADI Macro inspection system detects defects that appear after the photolithography development step and include regions of defocus ("hot spots"), scratches, pattern blemishes, large particles, (i.e., particles greater than about 25 micron minimum dimension range), extra deposited photoresist, nonuniform photoresist deposition, and edge bead removal inconsistencies. Two fluorescent lamp tubes are used to illuminate the target area in dark field, and one fluorescent lamp tube is used in an oblique configuration to illuminate the target area in bright field. First and second imaging systems collect, respectively, bright field light rays and dark field light rays propagating from the illuminated target area of the wafer surface. Each of two light sensor arrays optically communicates with a different one of the first and second imaging systems. The light sensor array outputs provide a stream of digital data that is processed by an imaging computer. Defect detection from these data is accomplished by analyzing a difference image among nearby reticle fields of the specimen wafer.

38 Claims, 11 Drawing Sheets

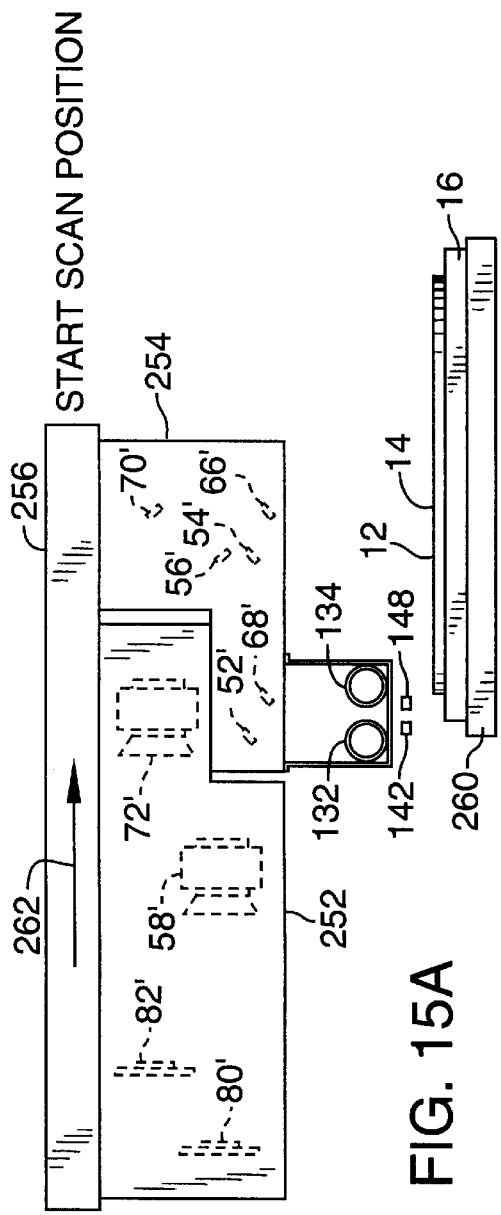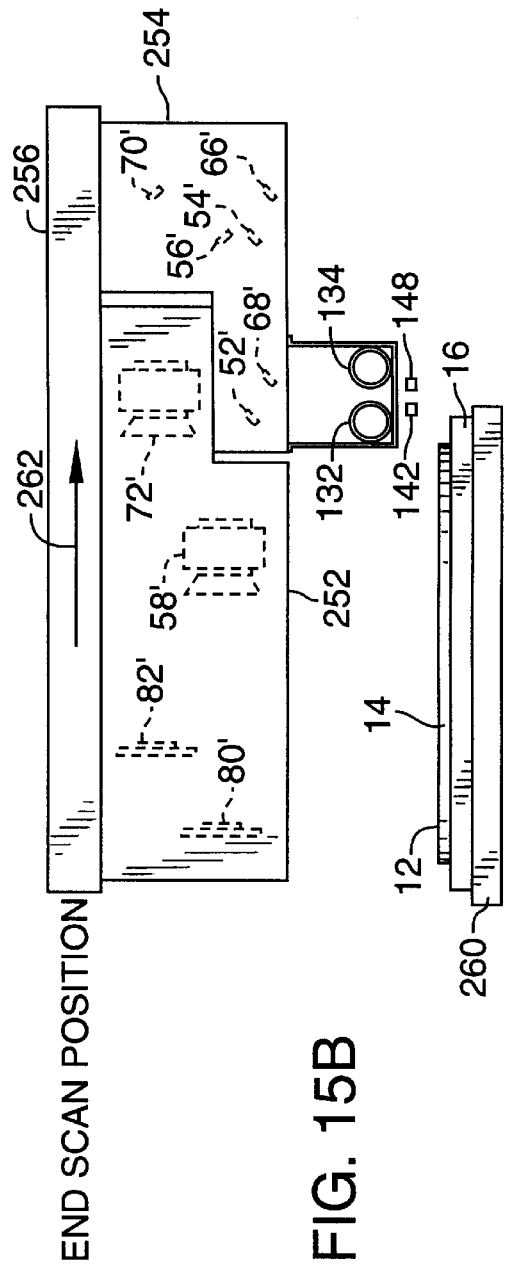

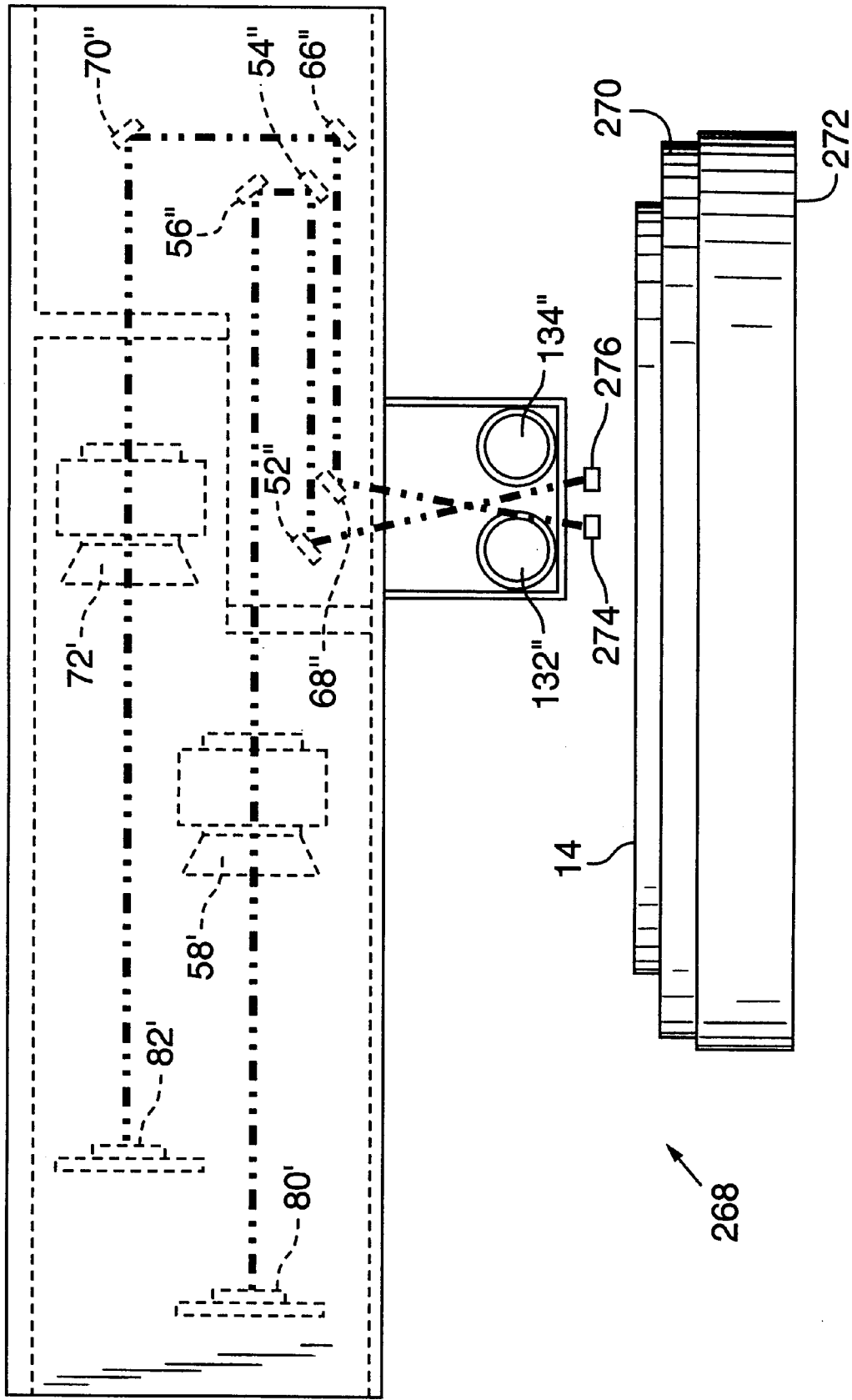

AUTOMATED SPECIMEN INSPECTION SYSTEM FOR AND METHOD OF DISTINGUISHING FEATURES OR ANOMALIES UNDER EITHER BRIGHT FIELD OR DARK FIELD ILLUMINATION

TECHNICAL FIELD

This invention relates to automated specimen inspection systems and methods and, in particular, to an automated system for and method of inspecting a surface of a specimen having distinguishing features or anomalies that are detectable under either one or a combination of bright field illumination and dark field illumination.

BACKGROUND OF THE INVENTION

The background description for this invention is presented only by way of example with reference to after develop inspection (ADI) for macro-size surface defects on a patterned or an unpatterned semiconductor wafer specimen.

The objective of macro-size defect inspection is to ensure that the wafer is free from yield-limiting large scale (i.e., greater than about 25 micron minimum dimension range) defects, such as incomplete or extra photoresist coverage, regions of defocus ("hot spots"), scratches, pattern blemishes, particles, and nonuniform or incomplete edge bead removal (EBR). With the exception of EBR, such defects appear on either a lot-to-lot (systematic) or a wafer-to-wafer (random) basis; therefore, a typical strategy is to inspect some or all wafers from each lot of wafers.

One popular way of performing ADI for macro-size defects entails placing the wafer on a semiautomatic tilt table and rotating the wafer through various angles under a bright light. U.S. Pat. No. 5,096,291 describes one type of semiautomatic tilt table that rotates a specimen about a central axis while positioning the specimen in different inclinations relative to a plane normal to the central axis. An operator visually inspects the wafer as it rotates and changes inclination and renders decisions about the presence or absence of defects. Wafers are either passed or rejected, based upon the operator's judgment. Defects very large in size in comparison to the minimum device design geometry dictate the degree of detection sensitivity required in connection with ADI for macro-size defects. This function is currently performed with the human eye aided by high intensity light in a dark field or bright field configuration. FIG. 1 shows five types of defects typically found during ADI for macro-size defects on a surface of a semiconductor wafer specimen.

With reference to FIG. 1, defect location A represents incomplete photoresist coverage; defect location B represents a surface scratch; defect location C represents extra deposited photoresist; defect location D represents a "hot spot"; and defect location E represents nonuniform edge bead removal. The term "hot spot" refers to a photoresist exposure anomaly caused by a depth of focus limitation or nonuniformity generally resulting from planar nonuniformity of the wafer at the time of exposure, the presence of foreign material on the backside of the wafer or on the wafer support system, or to a photolithography equipment problem or design constraint. The foreign material effectively deforms the wafer, which as a consequence presents a nonuniform focal surface during photolithography exposure. The existence of nonuniform focus during the photolithography process manifests itself as an unwanted pattern feature change.

Each of the defects identified above has a characteristic signature that manifests itself under either dark field or bright field illumination. Table 1 presents each such defect together with its characteristic signature produced under the appropriate illumination field.

TABLE 1

| Defect Type | Characteristic Signature Under Bright Field (BF) and Dark Field (DF) Illumination at Various Wafer Inclination Angles |
|---|---|
| Scratches | DF: Bright line on dark background |
| Incomplete photoresist coverage | BF: Thin film interference effects |
| Extra photoresist | BF: Thin film interference effects |
| Large defocus | DF: Dim or bright pattern compared to neighboring die |
| Nonuniform edge bead removal | BF: Nonuniform photoresist edge detected at the edge of the wafer |

Other defects or anomalies and distinguishing features having characteristic signatures under bright field and dark field illumination at various wafer inclination angles include no or partial exposure, large line width variations, overexposure, large particles, comets, striations, no photoresist deposited, underdeveloped photoresist, double exposure, development spots, and double development.

The high monetary value of each wafer makes this inspection strategy viable because the wafers generally can be reworked and abnormal process excursions can be readily detected and corrected. Lithography and automation trends in the industry are making ADI more critical and operator involvement less useful; therefore, an automated solution is needed.

SUMMARY OF THE INVENTION

An object of this invention is to provide an automated inspection system and method that replace human visual inspection of the surface of a specimen having distinguishing features or anomalies that are detectable under one or a combination of bright field illumination and dark field illumination.

An advantage of the invention is that it is capable of automatically and concurrently identifying and processing distinguishing features or anomalies, the characteristic signatures of which are revealed by either one or a combination of bright field illumination and dark field illumination. The invention detects the presence of, locates, classifies, and analyzes such distinguishing features or anomalies.

The present invention is an automated specimen inspection system and method that detect distinguishing features or anomalies under either one or a combination of bright field illumination and dark field illumination. The invention is especially useful for defect inspection of semiconductor wafer, thin-film magnetic head, flat panel display, chip carrier, microchip module (MCM), and micromachined specimens. A preferred embodiment is an ADI system that inspects the patterned surface of a semiconductor wafer for large scale (i.e., greater than about 25 micron minimum dimension range) defects. Defects of this size are sometimes called "macro-defects"; hence, the preferred embodiment described below is referred to as an "ADI Macro" inspection system for defects. It will be understood, however, that the invention is not restricted to defect inspection.

The ADI Macro inspection system is a high resolution, high throughput automatic semiconductor wafer inspection system that is intended to replace the human visual inspection of wafers currently taking place after the photolithography development step of the semiconductor wafer fabrication process. (This inspection system can, however, be used before or after any process step at any stage of the wafer fabrication process.) The inspection system can inspect an entire 200 millimeter photoresist-coated wafer in fewer than 60 seconds with about a 25 micron minimum resolution on the wafer. This processing speed is comparable to the speed at which the photolithography process takes place. The system detects and classifies defects that appear after the photolithography development step and include "hot spots," scratches, large particles, (i.e., particles greater than about 25 micron minimum dimension range), extra deposited photoresist, nonuniform photoresist deposition, and edge bead removal inconsistencies.

One implementation of the ADI Macro inspection system captures bright field and dark field images of the entire wafer simultaneously during the linear travel of the specimen wafer surface beneath illumination and imaging optics. Three commercially available fluorescent lamp tubes illuminate a target area of fixed size through which the specimen wafer passes. Two of the lamp tubes are used to illuminate the target area in dark field, and a single lamp tube is used in an oblique configuration to illuminate the target area in bright field. First and second imaging systems collect, respectively, bright field light rays and dark field light rays propagating from the illuminated target area of the wafer surface. Each of the two light sensor arrays optically communicates with a different one of the first and second imaging systems. Each light sensor array includes a high performance multi-element line scan sensor that is coupled into its corresponding imaging system by means of a suitable lens. The light sensor array outputs are combined serially and processed to provide a single stream of digital data that is directly coupled to a commercially available pipelined high-speed parallel processing imaging computer. Defect detection from these data is accomplished by analyzing a difference image among nearby reticle fields of the specimen wafer. (Although beneficial because it increases signal-to-noise ratio, difference analysis can be omitted for certain defects, such as scratches.) System control is provided by a microprocessor-based computer.

In a stand-alone configuration, an operator places a cassette of wafers or multiple wafer cassettes onto a loading platform. The ADI Macro inspection system automatically loads wafers from an input cassette and begins the inspection process using a predetermined recipe or inspection program. The system captures the bright field and dark field images of the entire specimen wafer in fewer than 60 seconds and determines the presence of, locates, and classifies defects on the wafer surface. The inspection results are displayed on a system monitor, printed, and/or transmitted to the factory automation system or a process monitoring analysis system. When integrated with processing equipment, the ADI Macro inspection system can operate and report independently or communicate with other equipment using a standard interface protocol.

The inspection system is useful in two principal modes of operation, viz, production and engineering modes. In the production mode, the system continuously inspects specimen wafers and determines the presence of as well as locates, classifies, and/or analyzes defects present on each specimen wafer. If the defects found on the specimen wafer are not within a user selected range, the inspection system either alerts an operator or a process engineer to the condition or uploads the defect information to a host computer in which a fault detection level is set. In the engineering mode, the system can be used to inspect specimen wafers and thereafter alter the inspection and test parameters to achieve the desired level of defect presence sensitivity on a real-time basis.

Additional objects and advantages of the present invention will be apparent from the following detailed description of preferred embodiments thereof, which proceeds with reference to the accompanying drawings.

BRIEF DESCRIPTION OF THE DRAWINGS

FIGS. 15A and 15B are side elevation views of the alternative embodiment of FIG. 14 showing the optical component support structure in position at, respectively, the start and end of a scan.

FIGS. 16A, 16B, and 16C are respective isometric, side elevation, and plan views of an alternative embodiment of the optical component support structure in which stationary optical components and short length light sources are adapted for image data acquisition to radially scan a specimen positioned on a rotating, but otherwise stationary table.

DETAILED DESCRIPTION OF PREFERRED EMBODIMENTS

Figure 1:
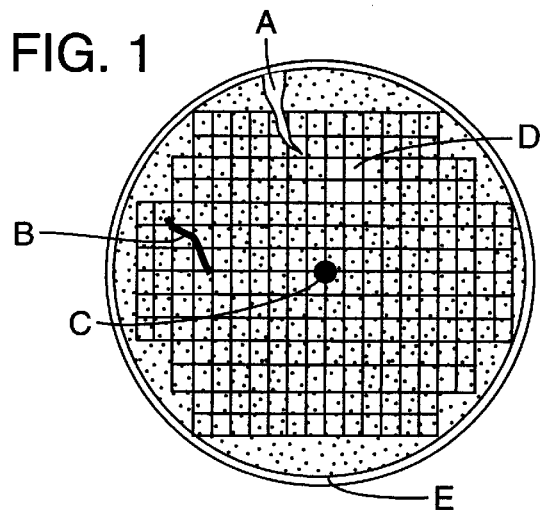
FIG. 1 is a plan view of the surface of a semiconductor wafer on which appear in different locations five types of defects typically found during ADI for macro-size defects.
Figure 2A:
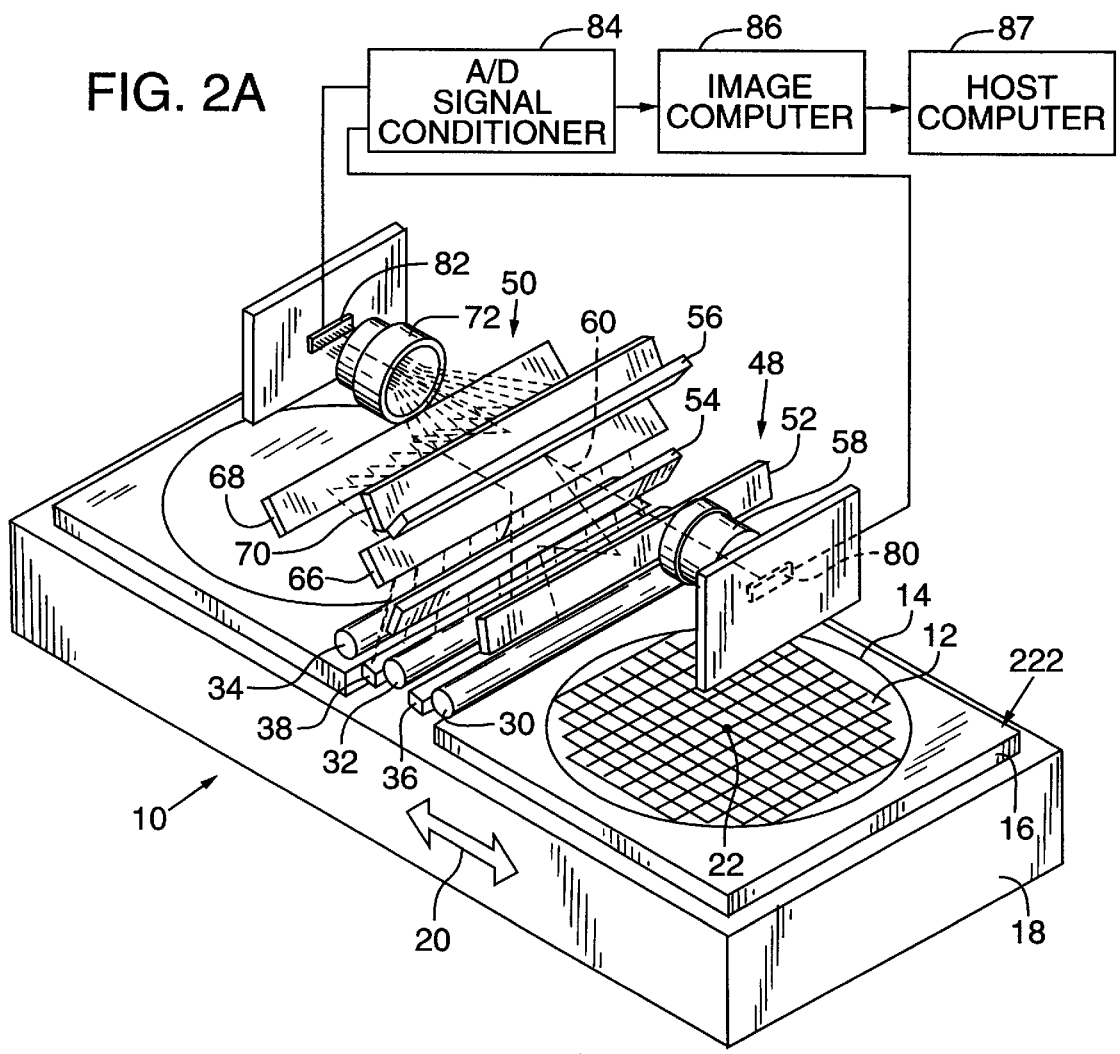
FIGS. 2A and 2B are isometric pictorial views of, respectively, the arrangement of and support structure for the optical components of a first preferred embodiment of an ADI Macro inspection system of the present invention.
Figure 2B:
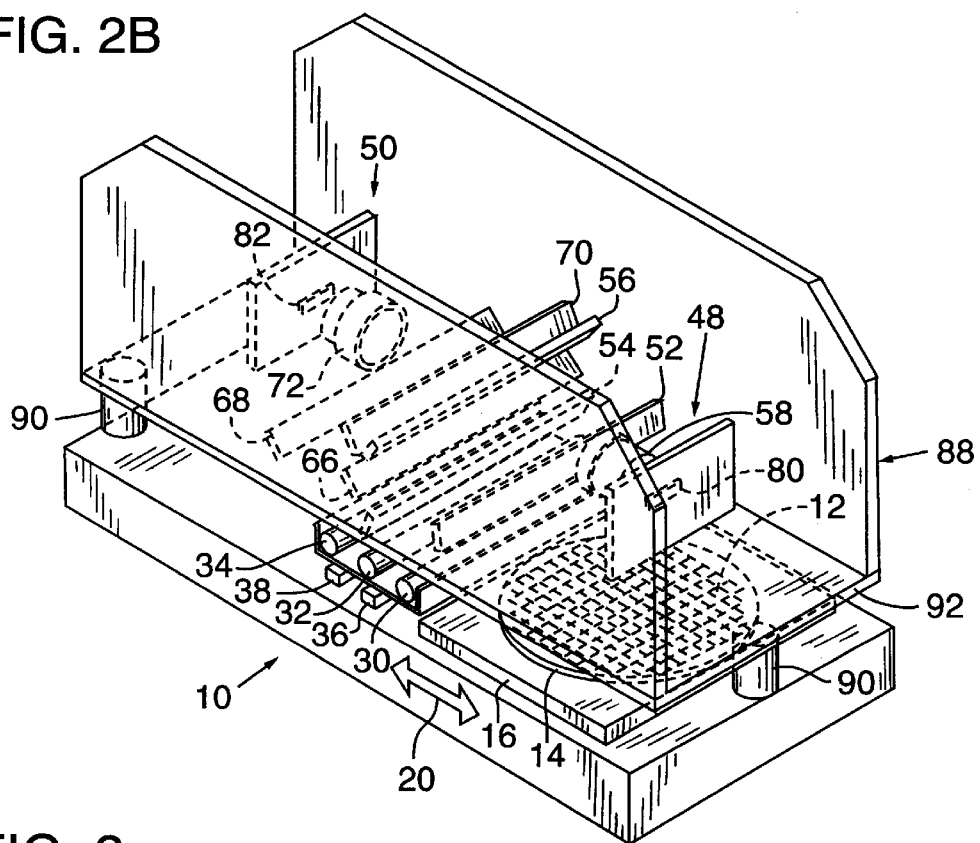
Figure 3:
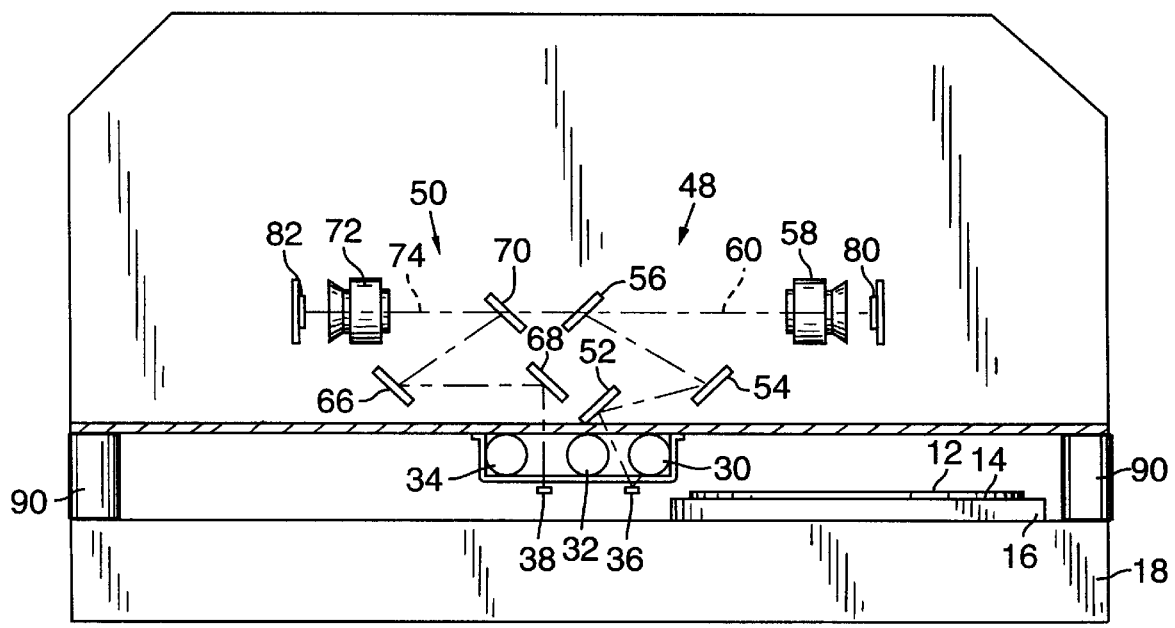
FIG. 3 is a side elevation view of the system of FIGS. 2A and 2B.

FIGS. 2A and 2B and FIG. 3 show respective isometric and side elevation views of a first preferred implementation of an ADI Macro inspection system 10 that inspects a patterned surface 12 of a semiconductor wafer specimen 14. With particular reference to FIGS. 2A and 3, wafer 14 is secured by a suitable specimen holder such as a vacuum chuck (not shown) to the upper surface of a table 16 that is part of a motorized linear translation stage 18. Table 16 is translatable in either direction along a scan axis 20 and rotatable about a central axis 22. One such commercially available motorized translation stage is a Model ST-SS-180-P200-R-H, manufactured by Pacific Precision Laboratories, Inc., Chatsworth, Calif. Table 16 is a simple traversing stage that transports wafer 14 at a constant velocity. A stepper motor (not shown) operating in a micro-stepped manner or a servomechanism-controlled DC motor (not shown) drives table 16. A conventional encoder (not shown) tracks the motion of table 16 to control the velocity and minimize position jitter of table 16 as it travels in either direction along scan axis 20.

Three stationary, elongate light sources 30, 32, and 34, which are preferably fluorescent lamp tubes, are positioned above and extend across the width of the upper surface of translation stage 18. Lamp tubes 30, 32, and 34 are spaced apart and cooperatively arranged to provide bright field and dark field illumination to surface 12 of wafer 14 as it travels beneath them. Lamp tube 30 is positioned to operate in an oblique mode and provides continuous illumination of a bright field scan area 36, and lamp tubes 32 and 34 cooperate to provide continuous illumination of a dark field scan area 38. (Skilled persons will appreciate that continuous illumination could also be achieved by a string of point sources positioned in optical association with a light diffusing element.) Each of scan areas 36 and 38 is fixed in space and extends across the entire patterned surface 12 of wafer 14 in a transverse direction to scan axis 20 as translation stage 18 transports wafer 14 during the data acquisition phase of the inspection process. A bright field imaging system 48 and a dark field imaging system 50 are positioned to collect light rays propagating from scan area 36 and scan area 38, respectively.

Bright field imaging system 48 includes light path directing elements or simple slit mirrors 52, 54, and 56 and an imaging lens 58. Mirrors 52, 54, and 56 are positioned to direct the bright field light rays propagating along a folded bright field path 60 to lens 58 after the light rays have struck surface 12 of wafer 14. Dark field imaging system 50 includes light path directing elements or simple slit mirrors 66, 68, and 70 and an imaging lens 72. Mirrors 66, 68, and 70 direct dark field light rays propagating along a folded dark field path 74 to lens 72 after the light rays have struck surface 12 of wafer 14. Skilled persons will appreciate that folding of the light paths is an optional implementation of the invention.

Imaging lenses 58 and 72 are fixed lenses that receive, respectively, the bright field light rays reflected by mirror 56 and the dark field light rays reflected by mirror 70. Each of imaging lenses 58 and 72 is a conventional, commercially available high quality industrial lens and operates at F#8 to reduce the optical aberrations present and minimize the effects of intensity fall-off at the edge of the imaging field. Skilled persons will appreciate that a variable magnification lens can be operated in a dynamic mode to fix the magnification desired for the specific specimen under inspection and detector configuration. Light sensitive sensors 80 and 82 are positioned behind the respective lenses 58 and 72, which concentrate the light passing through them on the light receiving surfaces of the sensors. Each of sensors 80 and 82 is preferably an 8,000 PN diode element line scan sensor array but may also be of a charge-coupled, time delay integration (TDI), or other suitable device type.

In a preferred implementation, lenses 58 and 72 each provide approximately a 3:1 reduction in magnification of light that strikes sensors 80 and 82 of a line scan sensor array type. A 72 millimeter line scan array, a 3:1 magnification enlarging lens, and 225 millimeter long mirrors in each of imaging systems 48 and 50 would adequately cover the patterned surface area of a standard 200 millimeter semiconductor wafer. A typical center-to-center spacing between scan areas 36 and 38 is 3.2 centimeters with the use of 16 millimeter diameter lamp tubes 30, 32, and 34.

The outputs of linear scan sensor arrays 80 and 82 are combined by an analog/digital signal conditioner 84 to form a single stream of digital data that is transmitted directly to the input of an image computer 86 for processing. Image computer 86 is preferably a commercially available parallel processing system used by the machine vision industry such as, for example, a model MaxPCI manufactured by DataCube, Inc., Danvers, Mass. A host computer 87 provides overall inspection system control and performs certain specified functions, such as for example receiving from image computer 86 defect information and comparing it against a pre-established fault detection level. The processing of bright field and dark field image data is described below with reference to FIGS. 7–13.

With reference to FIG. 2B, lamp tubes 30, 32, and 34 and the optical components associated with imaging systems 48 and 50 are supported within a housing 88 having a U-shaped cross section. Three kinematic mounting members 90 (only two shown) positioned near the side margins of a base 92 of housing 88 support housing 88 on the upper surface of table 16 at a height that sets the desired illumination distance between lamp tubes 30, 32, and 34 and scan areas 36 and 38.

Figure 4A:
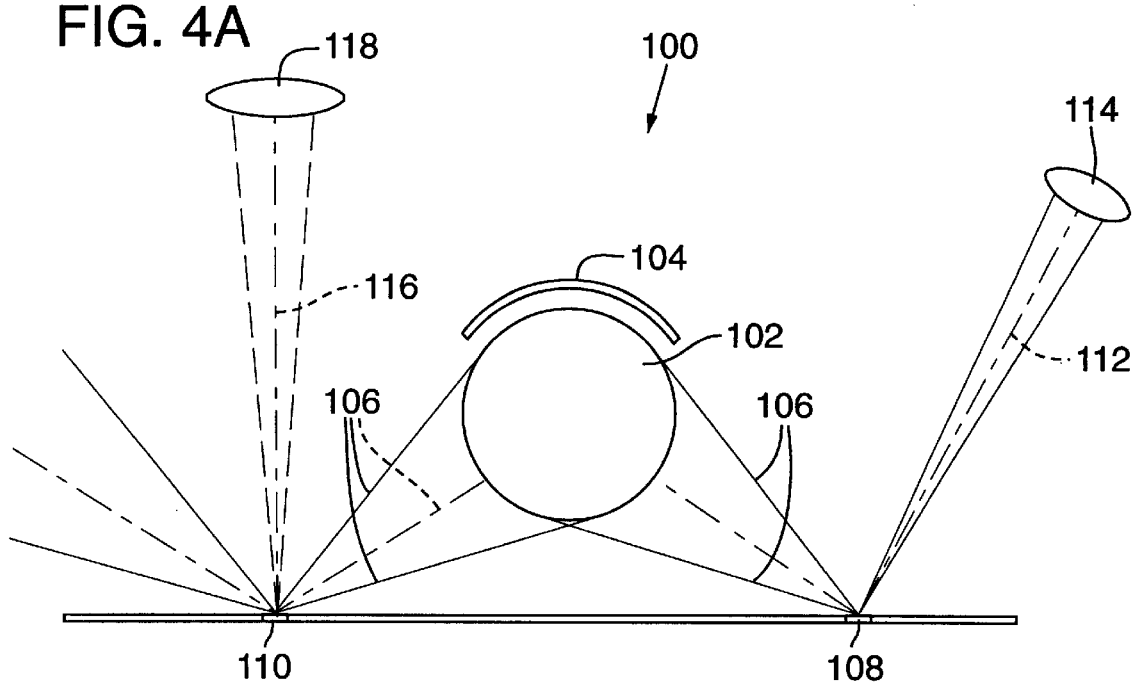
FIGS. 4A and 4B are schematic diagrams showing alternative illumination and imaging optics that include, respectively, one illumination source and two illumination sources for the use in an automated specimen inspection system of the present invention.
Figure 4B:
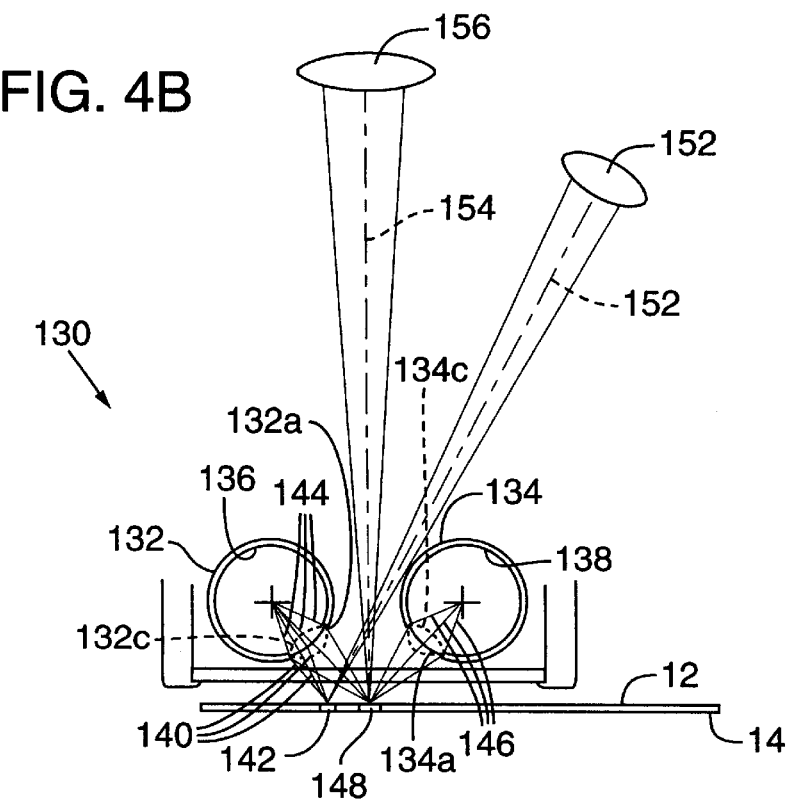

FIGS. 4A and 4B are schematic diagrams showing alternative illumination and imaging optics that include, respectively, one illumination source and two illumination sources for use in an automated specimen inspection system of the present invention. The light path folding mirrors have been removed for purposes of clarity. The two illumination source implementation of FIG. 4B provides the basis for a description with reference to FIGS. 5 and 6 of the principles underlying the dark field illumination of patterned surface 12 of wafer 14 for carrying out the invention.

With reference to FIG. 4A, a single illumination source inspection system 100 includes a single elongate light source 102 having either an internal or an external reflector 104 that directs light rays 106 to strike a bright field scan area 108 and a dark field scan area 110 on patterned surface 12 of wafer 14. Bright field light rays propagate along a path 112 after light rays 106 have struck bright field scan area 108 and then are collected by an imaging lens 114 that is positioned to receive specularly reflected light rays. Dark field light rays propagate along a path 116 after light rays 106 have struck dark field scan area 110 and then are collected by an imaging lens 118 that is positioned to receive nonzero order diffracted light rays. Because the dark field light rays are necessarily of diminished intensity, light source 102 is of a type that emits high intensity light rays 106 and is, therefore, an inherent disadvantage in the implementation of inspection system 100.

With reference to FIG. 4B, a two illumination source inspection system 130 includes two nominally identical elongate light sources 132 and 134 having either internal or external reflectors 136 and 138, respectively, that direct light to strike patterned surface 12 of wafer 14. Light sources 132 and 134 have respective apertures 132a and 134a through which light propagates. Light rays 140 propagating from source 132 strike a bright field scan area 142, and light rays 144 and 146 propagating from the respective light sources 132 and 134 strike a dark field scan area 148. Optional convex lenses 132c and 134c (shown in phantom lines) can be set in the respective apertures 132a and 134a to converge the light rays onto scan areas 142 and 148. Bright field light rays propagate along a path 150 after light rays 140 have struck bright field scan area 142 and are collected by an imaging lens 152 that is positioned to receive specularly reflected light rays. Dark field light rays propagate along a path 154 after light rays 144 and 146 have struck dark field scan area 148 and are collected by an imaging lens 156 that is positioned to receive specularly reflected light rays. The contributions of light rays 144 and 146 to illuminate dark field scan area 148 enhance the ability of inspection system 130 to detect defects with characteristic signatures under dark field illumination.

Figure 5A:
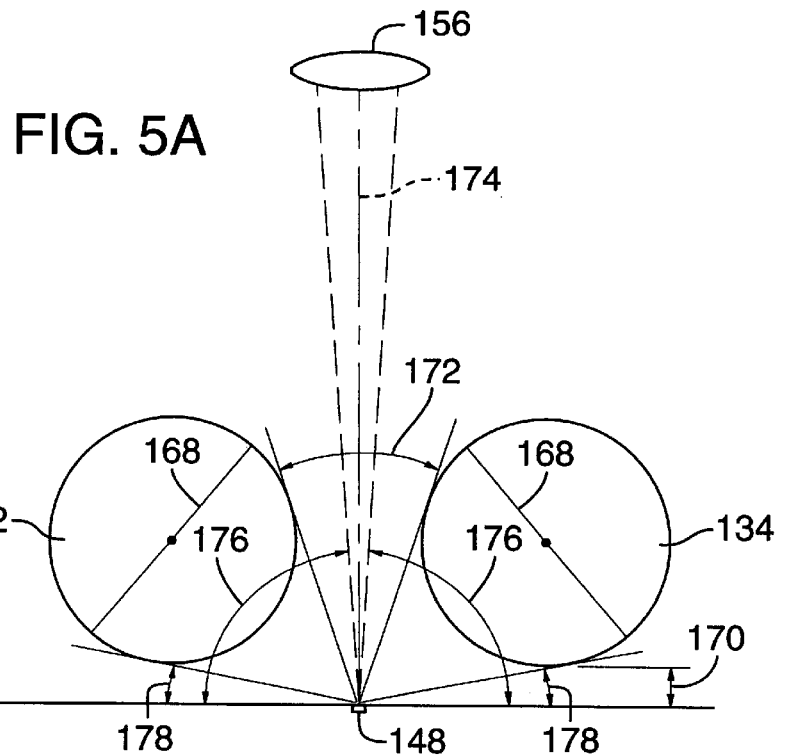
FIG. 5A is a diagram showing the parameters associated with selecting for dark field illumination the size and placement of the two light sources used in the system of FIG. 4B.

FIG. 5A is a diagram showing the parameters associated with selecting for dark field illumination the size and placement of light sources 132 and 134 of inspection system 130 (but is similarly applicable to light sources 32 and 34 of inspection system 10 shown in FIGS. 2 and 3). With reference to FIG. 5A, dark field scan area 148 is very much smaller than effective illumination surfaces 168 produced by light sources 132 and 134 to provide illumination of nearly uniform intensity of dark field scan area 148. The following is a numerical example that presents the pertinent optical design considerations for light sources 132 and 134 in the shape of cylindrical tubes.

For a 0.027 millimeter wide dark field scan area 148 and a 2.0 millimeter minimum clearance 170 of light sources 132 and 134 above patterned surface 12 of wafer 14, the envelope defined by 30° entrance angle 172 of imaging lens 156 dictates about a 19 millimeter tube diameter for each of light sources 132 and 134. The placement of the 19 millimeter diameter light sources 132 and 134 at points equidistant from a principal axis 174 of imaging lens 156 at the specified 2.0 millimeter clearance defines a 60° maximum acceptance angle 176, a 15° incident illumination envelope 178, and 19 millimeter effective illumination surfaces 168. Thus, a 19 millimeter effective illumination surface 168 is between two and three orders of magnitude greater than the 0.027 millimeter width of dark field scan area 148. Skilled persons will appreciate that selecting larger diameter light sources 132 and 134 would necessarily position them farther away from patterned surface 12 and thereby reduce the intensity of illumination directed toward dark field scan area 148. With reference to FIG. 4B, for the parameters specified above, the center-to-center distance between scan areas 142 and 148 is about 5 millimeters, apertures 132a and 134a are about 60°, and the distances between the outer surface of light source 132 and bright field scan area 142 and dark field scan area 148 are about 16 millimeters and 21 millimeters, respectively.

A relatively small dark field scan area 148 and relatively large effective illumination surfaces 168 cooperate to provide a consistent light intensity distribution angle, which is measured relative to principal axis 174 bisecting the width of dark field scan area 148. A lateral displacement or scan "walk off" on either side of principal axis 174 produces no appreciable diffracted light ray angle change (i.e., no chief ray walk) relative to the normal to dark field scan area 148.

The illumination energy is of sufficient intensity to maintain the image capturing speed and maximum image blur requirements. For a 15 mm/sec travel speed of table 16 along scan axis 20, the maximum exposure time is 500 microseconds at dark field scan area 148; and for a typical PN diode element line scan sensor 82, the saturation voltage is 5.5 volts. The line scan sensor at 550 nm has an average responsivity of 25 volts/($\mu$J/cm$^2$), and fluorescent lamp tubes 132 and 134 have an irradiance of approximately 0.02 watts/cm$^2$. Lamp tubes 132 and 134 are preferably used at an extremely close range. The approximate energy available for full exposure is expressed as $$\text{ExposureFactor} = \frac{\text{Responsivity}_{\text{ImagingSensor}} * M_{\text{MagnificationObject} \to \text{Image}}^2 * \text{Irradiance} * \text{ExposureTime}}{V_{\text{SaturationVoltage}}}$$

$$\text{ExposureFactor} = \frac{25 \text{ Volts}/(\mu J/cm^2) * 3^2 * 0.02 (\text{Watts}/cm^2) * 500 \; \mu\text{sec}}{5.5 \text{ Volts}} = 400.$$

An exposure factor of over 400 provides sufficient energy under dark field illumination with 4,096 gray levels and provides an overabundance of energy for bright field illumination.

Figure 5B:
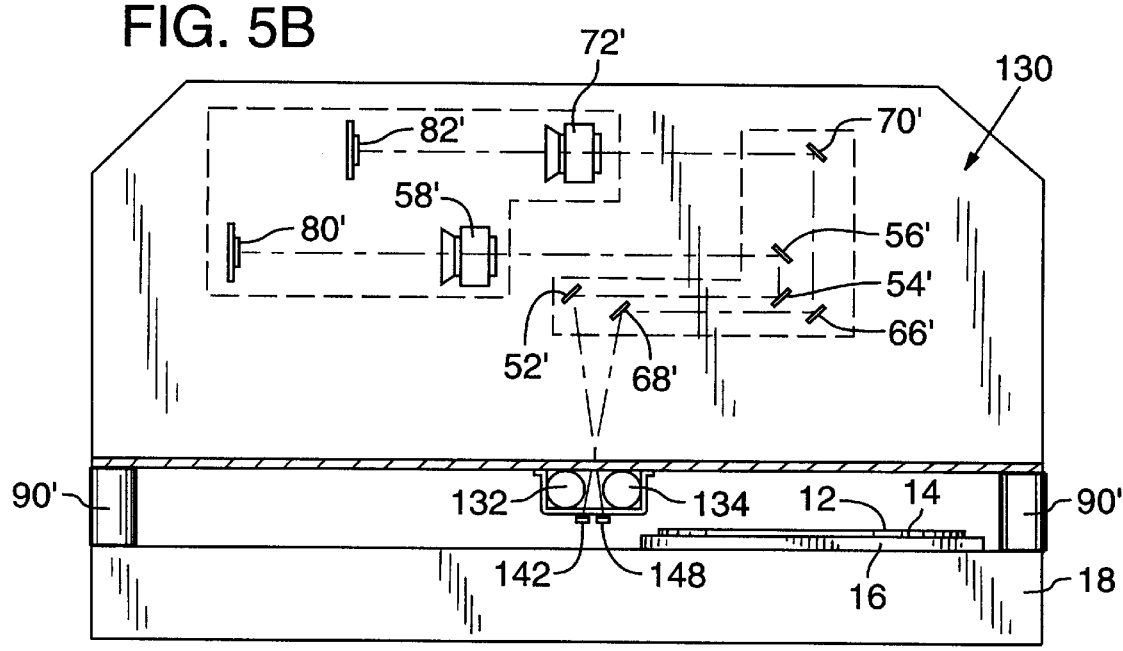
FIG. 5B is a side elevation view of the inspection system of FIG. 4B implemented as an ADI Macro inspection system.

FIG. 5B is a side elevation view of inspection system 130 implemented as an ADI Macro inspection system that, with the exception of the number of light sources, is analogous to inspection system 10 as shown in FIG. 3. Corresponding optical components of inspection systems 10 and 130 are identified by common reference numerals, with those of inspection system 130 followed by primes.

Figure 6:
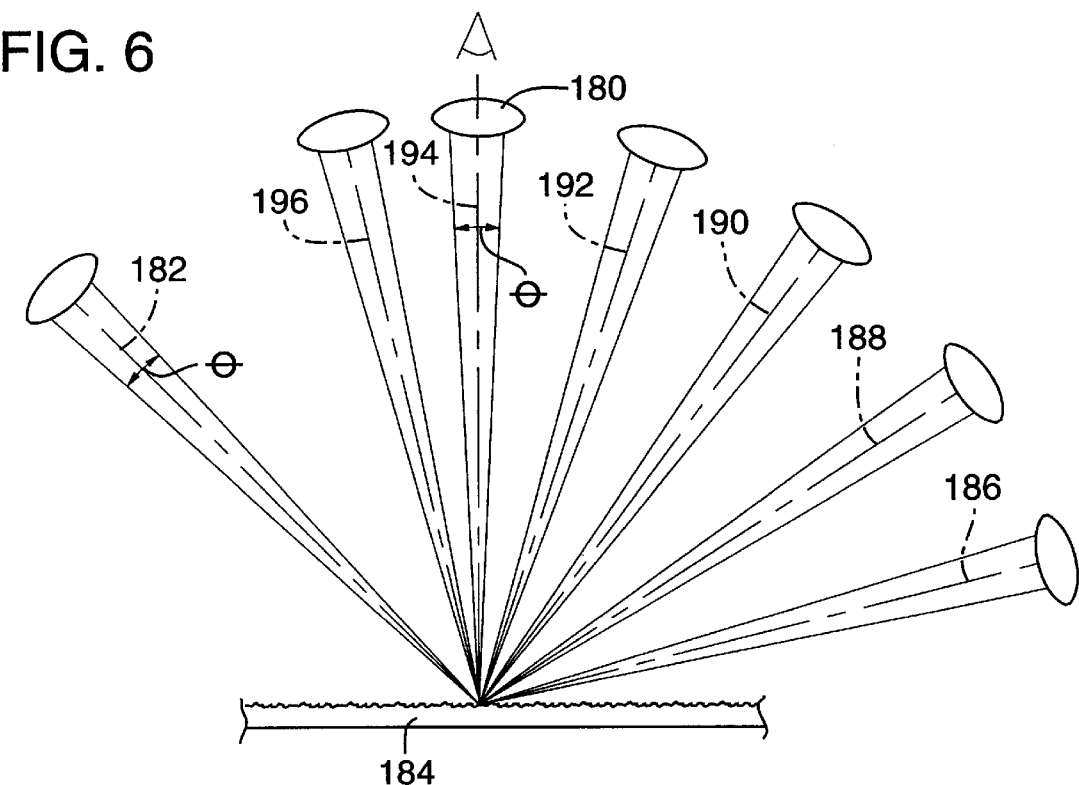
FIG. 6 is a diagram that shows the effect of the beam width of an incident beam on the amount of dark field light ray intensity collected by an imaging lens.

FIG. 6 is a diagram showing the effect of the beam width size of the incident beam on the amount of light collected by an imaging lens 180 collecting dark field light rays. With reference to FIG. 6, a unidirectional, single wavelength illumination beam 182 of angular beam width $\Theta$ strikes a diffraction grating 184 the periodicity of which produces a family of angularly spaced diffracted light beams 186, 188, 190, 192, 194, and 196 the intensities of which depend on their orders of diffraction. Because they are replicas of illumination beam 182, the diffracted light beams each have the illumination angular beam width $\Theta$.

Figure 7:
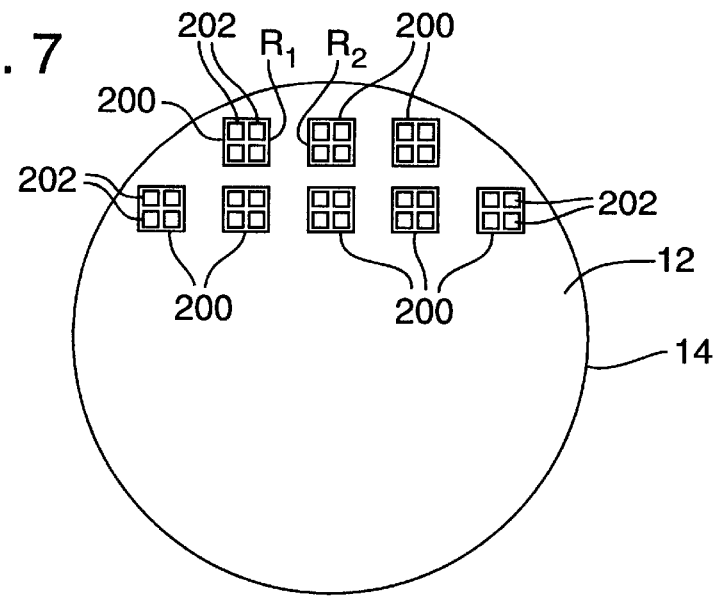
FIG. 7 shows the layout of a wafer pattern having multiple nominally identical reticle fields arranged in rows and columns.

ADI Macro inspection system 10 determines the presence of defects from the acquired image data of a specimen wafer 14 by analyzing the difference image of two adjacent reticle fields. FIG. 7 shows wafer 14 having a patterned surface 12 with eight reticle fields 200 in each of which there are four dice 202. For the example shown in FIG. 7, defects are detected by analyzing the difference image of adjacent reticle fields $R_1$ and $R_2$.

A 200 millimeter wafer 14 with a scanning density, S, of about 38 lines/millimeter requires a number of pixels per line, $N_p$, in which to maintain a square pixel. $N_p$ is expressed as $$N_p = 200 \times S = 7,600 = 7.6\ K.$$

The amount of buffer memory, B, required to store 25.4 millimeters of scanned information is $$B = S \times N_p = 38 \times 25.4 \times 7.6\ K \approx 7.4\ \text{Mbytes}.$$

Figure 8:
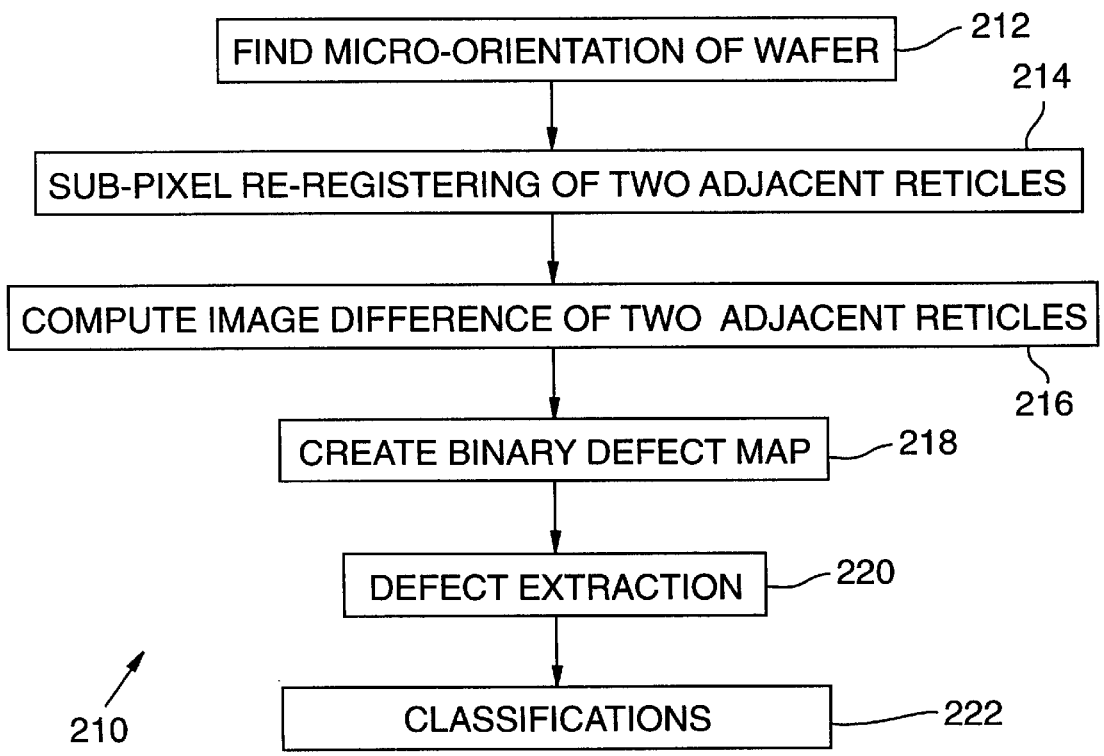
FIG. 8 is a flow diagram showing the processing steps for a scanned defect inspection algorithm for processing bright field and dark field imaging data acquired in accordance with the present invention.
Figure 9:
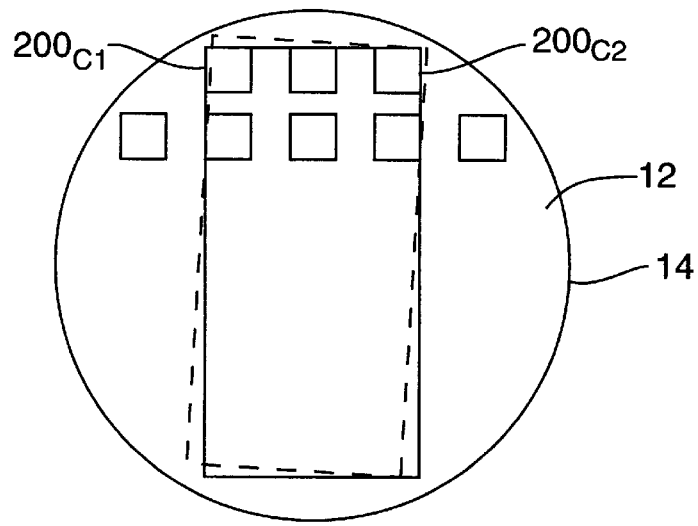
FIG. 9 is a diagram showing the angular offset of a wafer under inspection during prealignment preparatory to defect analysis.

FIG. 8 is a flow diagram showing the processing steps for a scanned defect inspection algorithm 210. The following description of defect inspection algorithm 210 is presented in conjunction with FIGS. 9–13. With reference to FIG. 8, process block 212 represents a determination of the microorientation of wafer 14 on the upper surface of table 16. Wafer 14 is assumed to be pre-aligned to within a close angular tolerance as shown in FIG. 9. Skilled persons will appreciate that prealignment of wafer 14 can be accomplished on translation stage 18 itself because of the presence of table displacement position sensors and the capability of table 16 to rotate about axis 22. An area of 3×2 reticle fields is processed by subsampling, thresholding, and blob analysis or other techniques to determine the positions of two corner reticle fields $200_{C1}$ and $200_{C2}$. The centroids of these corner reticle fields are computed and used as the geometric reference points of wafer 14 for subsequent processing.

Process block 214 represents a subpixel re-registering of two adjacent reticle fields. Process block 216 represents the computation of an image difference of two re-registered adjacent reticle fields. The difference between the adjacent reticle fields is compared to produce a gray level deviation map. Process block 218 represents the creation of a binary defect map of exceptional deviations. The process can entail simple thresholding on the gray level deviation map or a comparison of the gray level deviation map to a registered tolerance map. Process block 220 represents defect extraction, and process block 222 represents defect classification.

The inspection approach discussed above detects the defects on the difference image (absolute difference image is used to detect bright field and dark field defects) of two adjacent reticle field images (for example, $R_1$ and $R_2$ in FIG. 7). An ambiguity remains as to which reticle field ($R_1$ or $R_2$) actually contains the detected defects. To resolve this ambiguity, additional post-processing of the sets containing the defects detected in the difference images is carried out. A premise underlying the post-processing techniques is that the reticle field pattern feature is repeatable across all reticle fields 200 of a wafer 14, but the defects generally are not repeatable.

Figure 10:
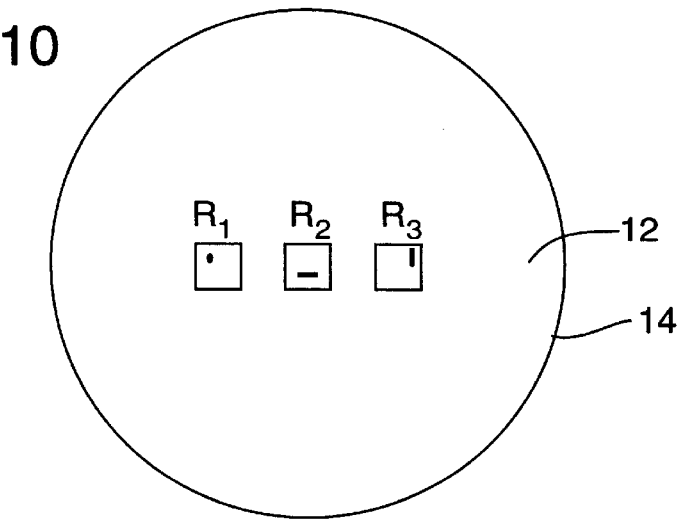
FIG. 10 is a diagram showing three wafer reticle fields having defects.
Figure 11:
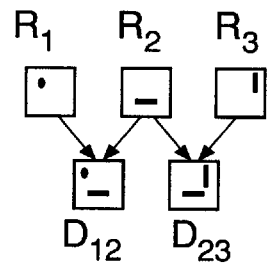
FIG. 11 shows the difference images formed by set intersection of two different pairs of next adjacent reticle fields of the three reticle fields of FIG. 10.

FIG. 10 shows three reticle fields $R_1$, $R_2$, and $R_3$, each of which has a defect. FIG. 11 shows the difference image $D_{12}$ of reticle fields $R_1$ and $R_2$, and the difference image $D_{23}$ of reticle fields $R_2$ and $R_3$.

The defect set of $D_{12}$ consists of a particle and a horizontal scratch and is expressed as:

$$d_{12} = \{\bullet, -\}.$$

The defect set of $D_{23}$ consists of a horizontal scratch and a vertical scratch and is expressed as:

$$d_{23} = \{-, |\}.$$

The set intersection of $d_{12}$ and $d_{23}$ produces the defect set $d_2$ of reticle field $R_2$ and is expressed as:

$$d_2 = d_{12} \cap d_{23}.$$

The set difference of $d_{12}$ and $d_2$ produces the defect set $d_1$ of reticle field $R_1$ and is expressed as:

$$d_1 = d_{12} - d_2.$$

(A technique for determining the defect set of edge reticle field $R_1$ is described below.)

In general, if there are n number of reticle field $\{R_j\}_{j=1}^n$ in a row of wafer 14, the defect set $\{d_j\}_{j=1}^n$ of all reticle fields on that row can be obtained as follows:

(a) The defect set $d_{ij}$ of the difference image $D_{ij}$ of two adjacent reticle fields $R_i$ and $R_j$ are computed as discussed above:

$$\{d_{ij}\} = \{d_{12}, \ldots, d_{n-1,n}\}.$$

(b) The defect set $d_j$ of reticle field $R_j$ is obtained by set intersection of the defect set $d_{ij}$ (of the difference image $D_{ij}$ of reticle fields $R_i$ and $R_j$) and the defect set $d_{jk}$ (of the difference image $D_{jk}$ of reticle fields $R_j$ and $R_k$):

$$d_j = d_{ij} \cap d_{jk} \text{ for } j = 2, \ldots, n-1.$$

(c) The defect set $d_i$ and $d_n$ of the two edge reticle fields (first and last reticle fields) $R_1$ and $R_n$ are obtained by set difference as follows:

$$d_1 = d_{12} - d_2$$

$$d_n = d_{n-1,n} - d_{n-1}.$$

Defects present in edge reticle fields are determined in the following manner.

Figure 12:
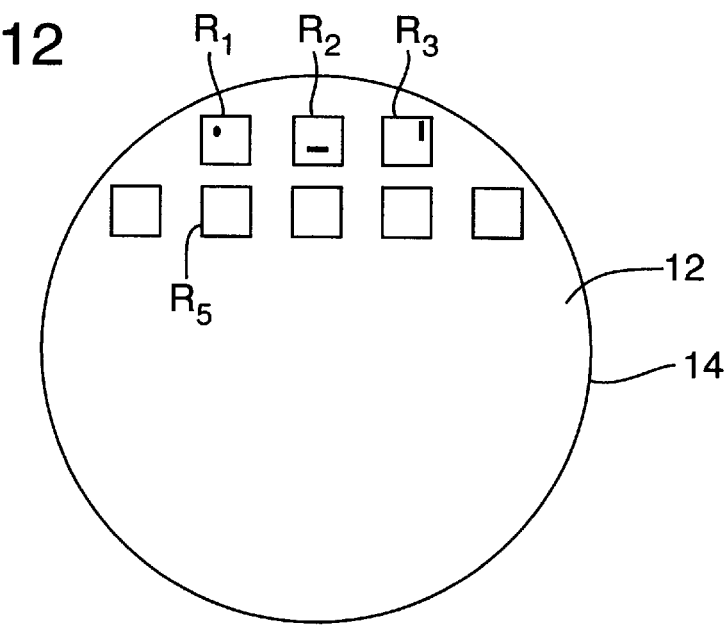
FIG. 12 is a diagram that is useful for describing defect determination for a reticle field located on the end of a row.
Figure 13:
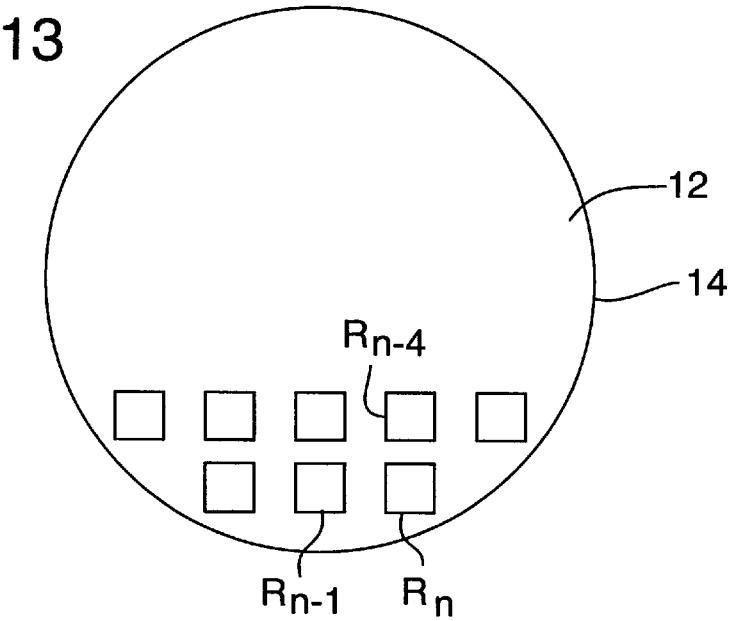
FIG. 13 is a diagram useful for describing defect determination of a reticle field located on the end of the last row of wafer reticle fields.

Each edge reticle field, for example, $R_1$, on a row has only one adjacent field on that row to derive one difference image. Another way to obtain the defect set of edge reticle field $R_1$ is to derive the second difference image of its adjacent reticle field $R_5$ on the next row, as shown in FIG. 12.

The defect set $d_1$ of $R_1$ is then obtained by set intersection of the defect set $d_{12}$ (of the difference image $D_{12}$ of reticle fields $R_1$ and $R_2$) and the defect set $d_{15}$ (of the difference image $D_{15}$ of reticle fields $R_1$ and $R_5$). The determination of the defect set $d_1$ is expressed as:

$$d_1 = d_{12} \cap d_{15}.$$

Both edge reticle fields (on the left end and the right end) of all rows can be handled as discussed above, except the last row. Defects present in edge reticle fields on the last row are determined in the following manner. For the edge reticle fields on the last row, for example reticle $R_n$ in FIG. 13, the second adjacent reticle field $R_{n-4}$ to derive the second difference image is present on the previous row, which is accessible immediately because the inspection scheme uses three buffers to store three reticle field rows of information.

There is minimum throughput overhead associated with the post-processing discussed above to determine what defects belong to which reticle field because the data to be processed (i.e., the number of defects in the difference images) are reduced substantially from the original raw image data and the post-processing can be accomplished by host or control computer 87.

ADI Macro inspection system 10 operates to acquire and process bright field and dark field image data as follows. Table 16 continuously moves wafer 14 along scan axis 20 from a load area 224 through bright field scan area 36 and dark field scan area 38 for a forward scan of patterned surface 12. Patterned surface 12 is effectively subdivided into swaths of uniform width equal to that of scan areas 36 and 38. Each swath of patterned surface 12 is sequentially illuminated at scan areas 36 and 38 to provide respective bright field image data and dark field image data, which are separately processed by image computer 86. Bright field and dark field image data corresponding to the same swath of patterned surface 12 are identified and correlated by the table 16 encoder position data. Defect detection post-processing in accordance with scanned defect inspection algorithm 210 on the acquired data is performed as different swaths of patterned surface 12 are illuminated at scan areas 36 and 38 for image data acquisition. Defects determined by post-processing of bright field and dark field image data represent defects with characteristic signatures under bright and dark field illumination, respectively.

Once it has reached the maximum distance from load area 224 so that image data acquisition is complete, table 16 is rotated 90° or any other angle about central axis 22 and reverses its movement along scan axis 20 back toward load area 224. During this reverse scan, bright field and dark field image data are again acquired and processed in the manner analogous to that described above. Rotating patterned surface 12 by 45° and reacquiring image data tends to eliminate aliasing effects caused by the rectilinear grid arrangement of the reticle fields 200 and thereby provides azimuthal filtering. A 45° rotation also provides good particle defect measurement results. Empirical data have shown that rotating patterned surface 12 by 90° and reacquiring image data can provide more defect information than that acquired during the forward scan. Other angles of rotation could be advantageous, depending on the circuit pattern of wafer 14.

Figure 14:
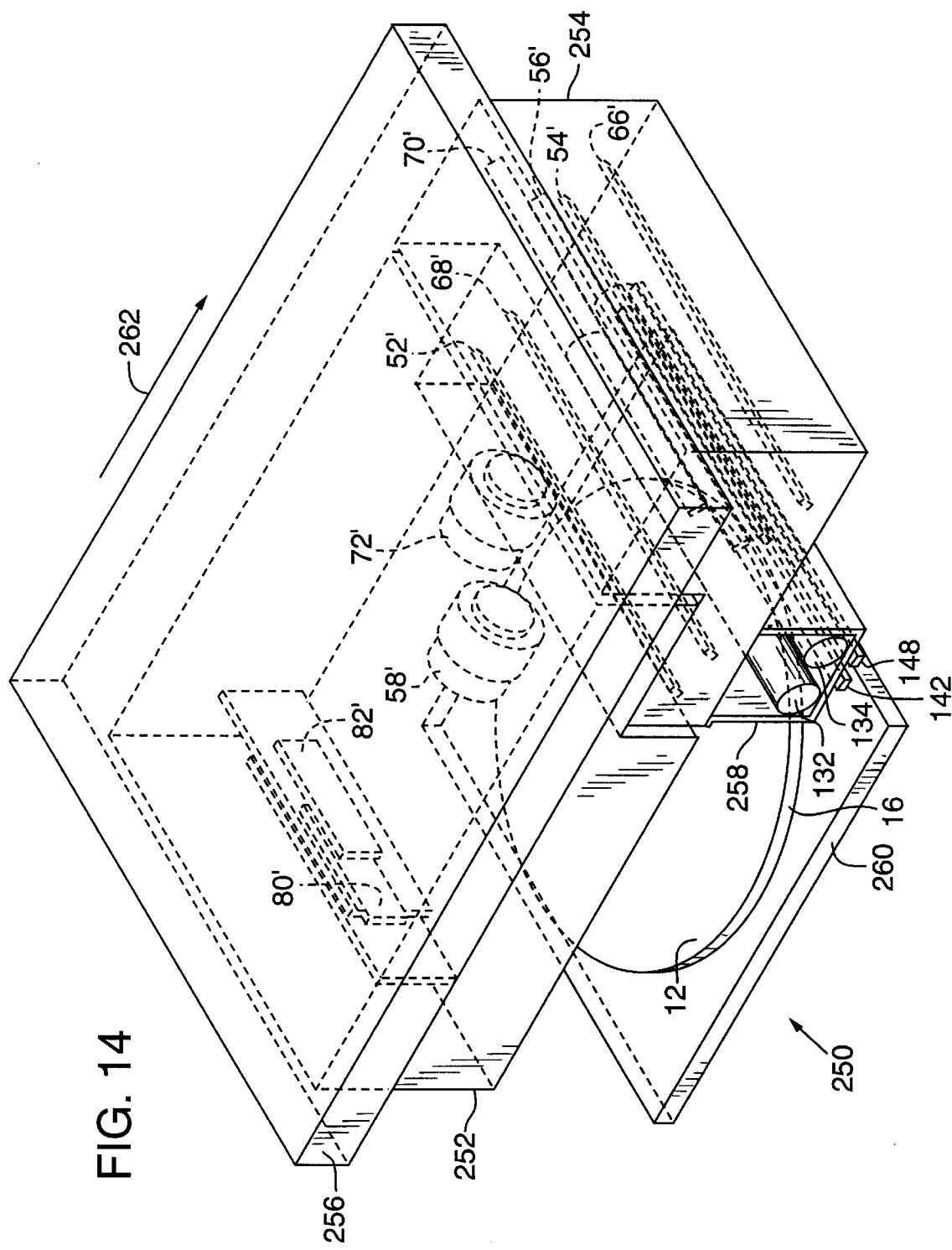
FIG. 14 is an isometric view of an alternative embodiment of the optical component support structure in which the optical components and light sources move to scan a specimen positioned on a rotatable table that is mounted on a stationary stage.

FIGS. 14, 15A, and 15B show an alternative inspection system embodiment 250 in which two illumination source inspection system 130 is modified such that the optical components are in fixed arrangement within housing modules 252 and 254 mounted to a motorized linear translation stage 256, light sources 132 and 134 are supported within a housing module 258 attached to housing module 254, and rotatable table 16 is mounted to a stationary stage 260. Housing module 252 supports light sensitive sensors 80' and 82' and imaging lenses 58' and 72' in their light path defined arrangements, and housing module 254 supports mirrors 66', 68', and 70' and mirrors 52', 54', and 56' in their light path defined arrangements.

As represented by FIGS. 15A and 15B, stage 256 moves module 254 along a scan axis 262 to accomplish a complete scan of wafer 14 mounted on table 16. Table 16 is rotatable about central axis 22, and stage 256 is capable of bidirectional motion along scan axis 262; therefore, specimen 14 can be scanned at different angles. Image data acquisition and processing are otherwise the same as was described above for inspection system 10.

Figure 16A:
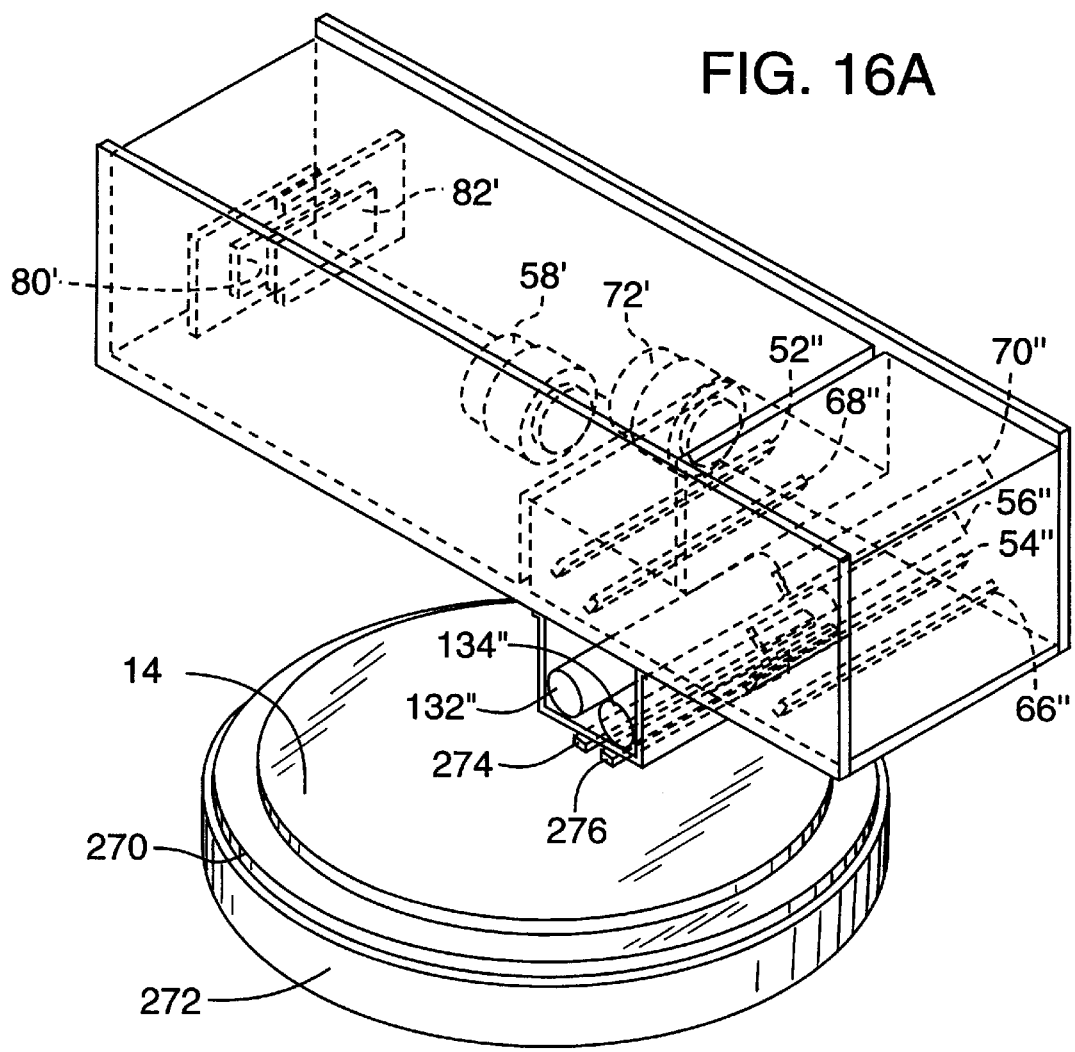
Figure 16C:
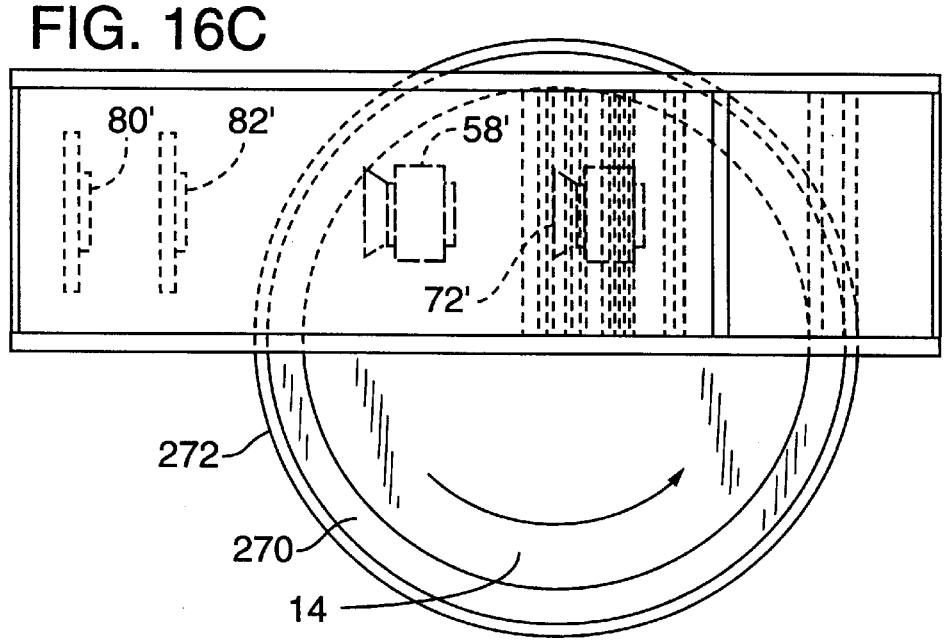

FIGS. 16A, 16B, and 16C show an alternative inspection system embodiment 268 in which two illumination source inspection system 130 is modified such that the lengths of the optical components and light sources are about equal to one-half of the longest dimension of a specimen 14 supported on a table 270 that is mounted to a motorized indexed rotation drive stage 272. Drive stage 272 is otherwise stationary. Thus, in the case of nearly circular wafer 14, mirrors 52", 54", 56", 66", 68", and 70" and light sources 132" and 134" correspond to and are about one-half the lengths of respective mirrors 52', 54', 56', 66', 68', and 70' and light sources 132 and 134. The lengths of the mirrors and light sources are about equal to the radius of wafer 14.

Image data acquisition is accomplished by repeating a linear scan of radial illuminated bright field scan area 274 and dark field scan area 276 for each rotational position of wafer 14 for 360° rotation of table 272. Image data processing is analogous to that described above for inspection system 10.

It will be obvious to those having skill in the art that many changes may be made in the above-described details of the preferred embodiments of the present invention without departing from the underlying principles thereof. As a first example, because defect or distinguishing feature size detection capability is directly proportional to the number of sensor elements per unit length in sensor arrays 80 and 82, the present invention implemented with a sensor array having a sufficiently high concentration of sensor elements per unit length can be used to detect submicron size defects or features. As a second example, multiple sensor arrays could be positioned end to end to provide an effectively longer detector that could also detect smaller defects or features. As a third example, the inspection system could be configured to acquire and process only dark field image information. As a fourth example, the inspection process could be accomplished with two passes of wafer 14 in coordination with an illumination switching sequence that provides dark field image information during one pass and bright field image information during the other pass. The scope of the present invention should, therefore, be determined only by the following claims.

I claim:

1. An automated method of inspection of a surface of a specimen having a length, a surface area, and distinguishing features or anomalies that are detectable under either bright field illumination or dark field illumination, comprising:

supporting the specimen in place on a support member;

directing light rays from at least two light sources of line illumination, each of which in optical association with a corresponding line aperture, to strike the surface of the specimen at angles of incidence that provide simultaneous bright field and dark field illumination of the specimen, the light sources positioned to illuminate at least two spaced-apart elongate scan areas;

imparting relative motion to the support member on which the specimen is supported in place and the light rays, the relative motion causing the light rays to traverse the surface of the specimen and leaving substantially unchanged the angles of incidence at which the light rays strike the surface, the length of the specimen defined in a transverse direction to the relative motion of the specimen and the light rays, and each of the scan areas extending along the length and being substantially less than the surface area of the specimen;

collecting at least some of the light rays after they have struck the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

2. The method of claim 1 in which the relative motion defines a direction and the transverse direction is perpendicular to the direction of relative motion.

3. An automated method of inspection of a surface of a specimen having distinguishing features or anomalies that are detectable under either bright field illumination or dark field illumination, comprising:

directing light rays from one or more light sources of line illumination, each of which in optical association with a corresponding line aperture, to strike the surface of the specimen at angles of incidence that provide simultaneous bright field and dark field illumination of the specimen, the light rays directed to strike the surface of the specimen illuminating first and second spaced-apart scan areas of the specimen;

imparting to the specimen and the light rays relative motion that causes the light rays to traverse the surface of the specimen and that leaves substantially unchanged the angles of incidence at which the light rays strike the surface;

collecting at least some of the light rays after they have struck the surface of the specimen, the collected light rays including bright field light rays propagating along a bright field path and dark field light rays propagating along a dark field path, and the collecting of light rays being accomplished by positioning a first set of multiple light path directing elements to receive and direct along a first path the bright field light rays and positioning a second set of multiple light path directing elements to receive and direct along a second path the dark field light rays, the first set of light path directing elements being positioned to receive bright field light rays propagating from the first scan area and the second set of light path directing elements being positioned to receive dark field light rays propagating from the second scan area; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

4. The method of claim 3 in which the specimen has a surface area and the light source or light sources illuminate a region of the surface area, the region being substantially larger than each of the first and second scan areas so that, for each of the first and second scan areas, the source or sources direct light rays that have about the same angles of incidence.

5. The method of claim 4 in which the angles of incidence of the light rays striking the first scan area are different from those of the light rays striking the second scan area.

6. An automated method of inspection of a surface of a specimen having a surface area and distinguishing features or anomalies that are detectable under either bright field illumination or dark field illumination, comprising:

directing light rays from one or more light sources of line illumination, each of which in optical association with a corresponding line aperture, to strike the surface of the specimen at angles of incidence that provide simultaneous bright field and dark field illumination of the specimen, the light rays directed to strike the surface of the specimen propagating from multiple stationary light sources of line illumination and the multiple stationary light sources of line illumination being positioned to illuminate first and second stationary spaced-apart elongate scan areas of the specimen;

imparting to the specimen and the light rays relative motion that causes the light rays to traverse the surface of the specimen and that leaves substantially unchanged the angles of incidence at which the light rays strike the surface, the specimen being mounted to a linear translation table that moves the specimen relative to the light sources of line illumination to cause the light rays to traverse the surface of the specimen, the table moving the specimen so that the first and second scan areas scan the entire surface area of the specimen;

collecting at least some of the light rays after they have struck the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

7. An automated method of inspection of a surface of a specimen having distinguishing features or anomalies that are detectable under dark field illumination, comprising:

supporting the specimen in place on a support member;

providing an illumination system from which light rays propagate to strike the surface of the specimen at angles of incidence that provide dark field illumination of a scan area of the specimen, the illumination system having an effective illumination surface and the scan area having a width, the effective illumination surface being substantially larger than the scan area so that the light rays striking the scan area provide illumination of substantially uniform intensity across the width of the scan area;

imparting relative motion to the support member on which the specimen is supported in place and the light rays, the relative motion causing the light rays to traverse the surface of the specimen and leaving substantially unchanged the angles of incidence at which light rays strike the surface;

collecting at least some of the light rays after they have struck the surface of the specimen, the collected light rays including dark field light rays propagating along the dark field path; and processing the dark field light rays to detect specimen features or anomalies having characteristic signatures under dark field illumination.

8. The method of claim 7 in which the collecting of light rays is accomplished by positioning a set of multiple light path directing elements to receive and direct the dark field light rays along a path.

9. The method of claim 8 in which the illumination system comprises at least one light source positioned to illuminate a scan area of the specimen, the set of light path directing elements being positioned to receive dark field light rays propagating from the scan area.

10. A specimen inspection system for detecting a distinguishing feature or anomaly, comprising:

a specimen support including a table for holding in place a specimen under inspection having a surface;

an illumination system from which light rays propagate, the illumination system having an effective illumination surface and being positioned relative to the surface of the specimen so that light rays strike the surface of the specimen at angles of incidence that provide dark field illumination of a scan area of the specimen, the effective illumination surface being substantially larger than the scan area so that the light rays striking the scan area have no appreciable difference in light intensity or light intensity distribution angle;

a mechanism for imparting to the table holding the specimen in place and illumination system relative motion that causes the light rays to traverse the surface of the specimen and that leaves substantially unchanged the angles of incidence at which the light rays strike the surface;

a light collecting system for collecting dark field light rays propagating from the scan area as the light rays traverse the surface of the specimen; and a processor for determining from the dark field light rays the presence of a specimen feature or anomaly having a characteristic signature under dark field illumination.

11. The system of claim 10 in which the illumination system includes multiple stationary light sources each having an effective illumination surface and in which the specimen support includes a rotatable table that moves the specimen relative to the light sources to cause the light rays to traverse the surface of the specimen.

12. The system of claim 10 in which the light collecting system includes a light sensitive sensor to detect the presence of the specimen feature or anomaly.

13. The system of claim 12 in which the light sensitive sensor includes a sensor array.

14. The system of claim 12 in which an image lens is positioned to receive the collected light rays before they reach the light sensitive sensors.

15. The system of claim 10 in which the scan area constitutes a first scan area and in which the light collecting system further collects bright field light rays propagating from a second scan area of the surface of the specimen and further comprises multiple light sensitive sensors to detect from the bright field light rays and the dark field light rays the presence of the specimen feature or anomaly.

16. The system of claim 10 in which the light rays directed by the illumination system to strike the surface of the specimen propagate from at least one source positioned proximal to the surface of the specimen.

17. The system of claim 10 in which the specimen has a length and a surface area and in which the illumination system includes at least two sources positioned to illuminate two spaced-apart scan areas, the length of the specimen defined in a transverse direction to the relative motion of the specimen held in place on the table and the light rays, and each of the scan areas extending along the length and being substantially less than the surface area of the specimen.

18. The system of claim 17 in which the angles of incidence of the light rays striking the first scan area are different from those of the light rays striking the second scanned area.

19. The system of claim 10 in which the illumination system includes multiple stationary sources each having an effective illumination surface and in which the table on which the specimen is held in place comprises a linear translation table that moves the specimen relative to the light sources to cause the light rays to traverse the surface of the specimen.

20. The system of claim 10 in which the processor determines from the dark field light rays the presence of a specimen feature or anomaly by comparing the dark field defect information against a pre-established reference stored in a database.

21. An automated method of inspection of a surface of a specimen having distinguishing features or anomalies that are detectable under either bright field illumination or dark field illumination, comprising:

supporting the specimen in place on a support member;

directing light rays from one or more light sources of line illumination, each of which in optical association with a corresponding line aperture, to strike the surface of the specimen at angles of incidence that provide simultaneous bright field and dark field illumination of the specimen, and at least one of the light sources comprises multiple light emitters in optical association with a light diffusing element;

imparting relative motion to the support member on which the specimen is supported in place and the light rays, the relative motion causing the light rays to traverse the surface of the specimen and leaving substantially unchanged the angles of incidence at which the light rays strike the surface;

collecting at least some of the light rays after they have struck the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

22. An automated method of inspection of a surface of a specimen having distinguishing features or anomalies that are detectable under either bright field illumination or dark field illumination, comprising:

supporting the specimen in place on a support member;

directing light rays to strike the surface of the specimen at angles of incidence that provide simultaneous bright field and dark field illumination of the specimen;

imparting relative motion to the support member on which the specimen is supported in place and the light rays, the relative motion causing the light rays to traverse the surface of the specimen and leaving substantially unchanged the angles of incidence at which the light rays strike the surface;

collecting at least some of the light rays after they have struck the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information, the processing including comparing the bright field and dark field specimen feature or anomaly information against a pre-established detection level stored in a database.

23. The method of claim 22 in which the specimen is a semiconductor wafer that includes multiple reticle fields having repeatable pattern features across the multiple reticle fields, the comparing bright field and dark field specimen feature or anomaly information including computing an image difference between two of the reticle fields and forming from the image difference a gray level deviation map for comparison against a gray level standard.

24. The method of claim 23 in which the gray level standard includes a threshold level or a tolerance map corresponding to the reticle field pattern features.

25. An automated method of inspection of a surface of a specimen having distinguishing features or anomalies that are detectable under either bright field illumination or dark field illumination, comprising:

supporting the specimen in place on a support member;

directing light rays to strike the surface of the specimen at angles of incidence that provide simultaneous bright field and dark field illumination of the specimen, the surface having a surface area and the light rays striking a region of the surface area;

imparting relative motion to the support member on which the specimen is supported in place and the light rays, the relative motion causing the light rays to traverse the surface of the specimen, a quantity of the light rays striking the region of the surface area forming a scan area that is substantially smaller than the region of the surface area so that the angles of incidence of the quantity of the light rays are about the same, and the relative motion leaving substantially unchanged the angles of incidence at which the quantity of the light rays forming the scan area strike the surface;

collecting at least some of the quantity of the light rays after they have struck the scan area of the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

26. The method of claim 25 in which the scan area constitutes a first scan area, the specimen has a length, and at least two light sources of line illumination direct the light rays to strike the surface of the specimen and to illuminate the first scan area and a second scan area, the length of the specimen defined in a transverse direction to the relative motion of the specimen and the light rays, and each of the first and second scan areas extending along the length and being substantially less than the surface area of the specimen.

27. The method of claim 26 in which the relative motion defines a direction and the transverse direction is perpendicular to the direction of relative motion.

28. The method of claim 26 in which the angles of incidence of the light rays striking the first scan area are different from those of the light rays striking the second scan area.

29. The method of claim 26 in which the relative motion defines a direction and the transverse direction is perpendicular to the direction of relative motion.

30. The method of claim 26 in which the angles of incidence of the light rays striking the first scan area are different from those of the light rays striking the second scan area.

31. The method of claim 25 in which the bright field and dark field light rays strike respective first and second light sensitive sensors to detect the presence of large scale features or anomalies.

32. The method of claim 31 in which first and second image lenses are positioned to receive the collected light rays before they reach the respective first and second light sensitive sensors.

33. The method of claim 25 in which the scan area constitutes a first scan area, the specimen has a length, and at least two light sources of line illumination direct the light rays to strike the surface of the specimen and to illuminate the first scan area and a second scan area, the length of the specimen defined in a transverse direction to the relative motion of the specimen and the light rays, and each of the first and second scan areas extending along the length and being substantially less than the surface area of the specimen.

34. An automated method of inspection of a surface of a specimen that includes multiple reticle fields having repeatable pattern features across the multiple reticle fields, the specimen having distinguishing features or anomalies that are detectable under either bright field illumination or dark field illumination, comprising:

directing light rays to strike the surface of the specimen at angles of incidence that provide simultaneous bright field and dark field illumination of the specimen;

imparting to the specimen and the light rays relative motion that causes the light rays to traverse the surface of the specimen and that leaves substantially unchanged the angles of incidence at which the light rays strike the surface;

collecting at least some of the light rays after they have struck the surface of the specimen, the collected light rays including bright field light rays propagating along a bright field path and dark field light rays propagating along a dark field path; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information, the processing including comparing the bright field and dark field specimen feature or anomaly information against a pre-established detection level stored in a database by computing an image difference between two of the reticle fields and forming from the image difference a gray level deviation map for comparison against a gray level standard.

35. The method of claim 34 in which the specimen is a semiconductor wafer.

36. The method of claim 34 in which the gray level standard includes a threshold level or a tolerance map corresponding to the reticle field pattern features.

37. An automated method of inspection of a surface of a specimen having distinguishing features or anomalies that are detectable under either bright field illumination or dark field illumination, comprising:

directing light rays to strike the surface of the specimen at angles of incidence that provide simultaneous bright field and dark field illumination of the specimen, the surface having a surface area and the light rays striking a region of the surface area;

imparting to the specimen and the light rays relative motion that causes the light rays to traverse the surface of the specimen, a quantity of the light rays striking the region of the surface area forming a scan area that is substantially smaller than the region of the surface area so that the angles of incidence of the quantity of the light rays are about the same, and the relative motion leaving substantially unchanged the angles of incidence at which the quantity of the light rays forming the scan area strike the surface;

collecting at least some of the quantity of the light rays after they have struck the scan area of the surface of the specimen, the collected light rays including bright field light rays propagating along a bright field path and striking a first light sensitive sensor and dark field light rays propagating along a dark field path and striking a second light sensitive sensor; and processing the bright field light rays to detect features or anomalies having characteristic signatures under bright field illumination and processing the dark field light rays to detect dark field features or anomalies having characteristic signatures under dark field illumination to thereby merge bright field and dark field specimen feature or anomaly information.

38. The method of claim 37 in which first and second image lenses are positioned to receive the collected light rays before they reach the respective first and second light sensitive sensors.

* * * * *